United States Patent
Alden

(10) Patent No.: US 9,750,578 B2
(45) Date of Patent: Sep. 5, 2017

(54) SURGICAL INSTRUMENT ACTUATION INPUT MECHANISMS, AND RELATED DEVICES, SYSTEMS, AND METHODS

(71) Applicant: INTUITIVE SURGICAL OPERATIONS, INC., Sunnyvale, CA (US)

(72) Inventor: Donald Alden, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 68 days.

(21) Appl. No.: 14/659,836

(22) Filed: Mar. 17, 2015

(65) Prior Publication Data

US 2015/0257744 A1    Sep. 17, 2015

Related U.S. Application Data

(60) Provisional application No. 61/954,165, filed on Mar. 17, 2014.

(51) Int. Cl.
| | | |
|---|---|---|
| *A61B 19/00* | (2006.01) | |
| *A61B 34/30* | (2016.01) | |
| *A61B 17/00* | (2006.01) | |
| *A61B 90/80* | (2016.01) | |
| *A61B 90/00* | (2016.01) | |

(52) U.S. Cl.
CPC ............ *A61B 34/30* (2016.02); *A61B 90/80* (2016.02); *A61B 2017/00477* (2013.01); *A61B 2090/0813* (2016.02)

(58) Field of Classification Search
CPC ... A61B 34/30; A61B 34/35; A61B 2034/302; A61B 2034/301

USPC .......................................................... 606/130
See application file for complete search history.

(56) References Cited

U.S. PATENT DOCUMENTS

| | | |
|---|---|---|
| 2013/0325031 A1 | 12/2013 | Schena et al. |
| 2013/0325033 A1 | 12/2013 | Schena et al. |
| 2014/0165770 A1* | 6/2014 | Abri .................. G06F 3/016 74/490.01 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Robert N Wieland
(74) *Attorney, Agent, or Firm* — Jones Robb, PLLC

(57) ABSTRACT

An actuation input mechanism for a teleoperated surgical instrument may include an interface structure and a shaft connected to the interface structure. The interface structure may be engageable with a drive structure of an actuation interface assembly of a teleoperated surgical system to be driven by the drive structure. The shaft may be rotatable in response to the interface structure being driven. The interface structure may comprise a depression shaped and sized to receive a fingertip. The interface structure may further comprise one or more gripping features disposed in the depression. A surgical instrument for a teleoperated surgical system may include an instrument shaft, an end effector, and a force transmission mechanism. The force transmission mechanism may comprise an actuation input mechanism to transmit drive forces to actuate the surgical instrument, the actuation input mechanism including an interface structure and a shaft.

29 Claims, 12 Drawing Sheets

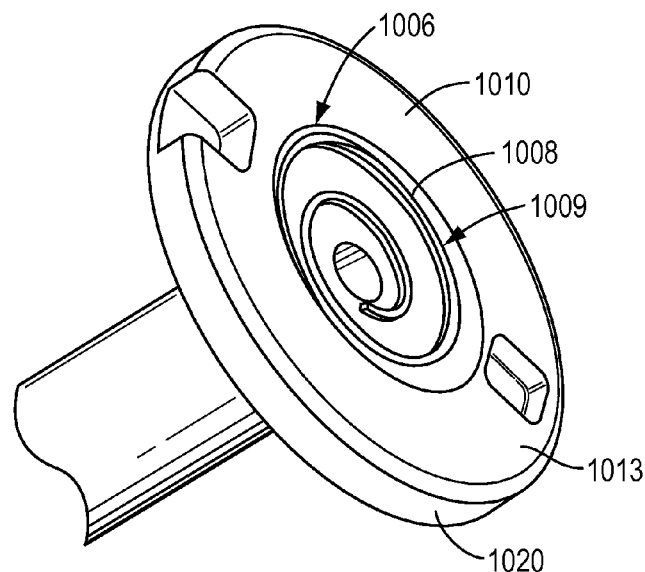
FIG. 18
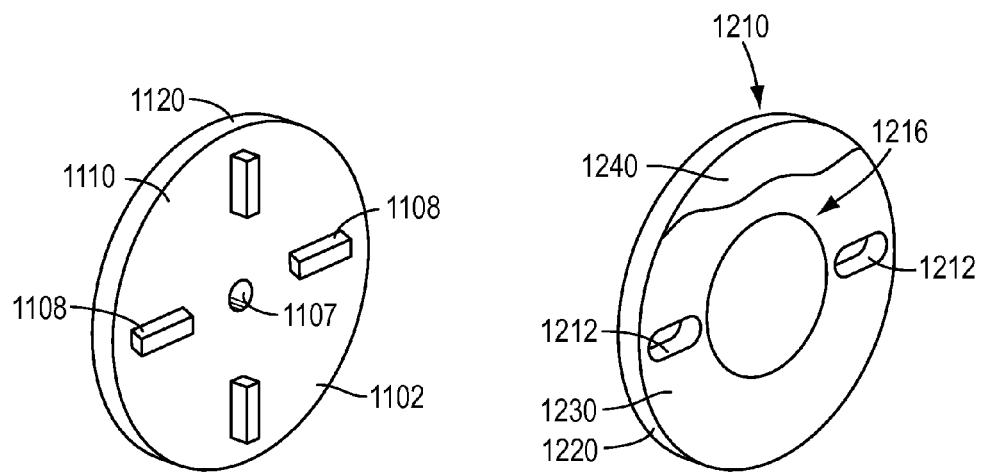
FIG. 19
FIG. 20

SURGICAL INSTRUMENT ACTUATION INPUT MECHANISMS, AND RELATED DEVICES, SYSTEMS, AND METHODS

This application claims the benefit of U.S. Provisional Application No. 61/954,165, filed on Mar. 17, 2014, which is incorporated by reference herein in its entirety.

TECHNICAL FIELD

Aspects of the present disclosure relate to surgical instrument actuation input mechanisms, and related devices, systems, and methods.

BACKGROUND

Remotely controlled surgical instruments, which can include teleoperated surgical instruments as well as manually operated (e.g., laparoscopic, thorascopic) surgical instruments, are often used in minimally invasive medical procedures. During a surgical procedure, a surgical instrument can come into contact with bodily fluids and other non-sterile substances and/or surfaces. After the surgical procedure, the surgical instrument may be cleaned. During the cleaning process, a user may wish to actuate various components, such as an end effector and/or wrist, of the surgical instrument to expose surfaces for access during cleaning. To actuate such components during the cleaning operation, the user may have to grip and manually actuate the component because the instrument is not attached to a surgical system that would normally provide an actuation input through a connected transmission housing of the surgical instrument. Gripping the component, however, may not be desirable because the component may include sharp surfaces, such as when the component is an end effector including scissors, a scalpel, or a blade, etc.

While cleaning procedures have been effective for cleaning surgical instruments, still further improvements to facilitate surgical instrument cleaning are desirable. For example, it may be desirable to facilitate actuation of various components, such as end effectors and/or wrists, of a surgical instrument by a user during a cleaning procedure.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, an actuation input mechanism for a teleoperated surgical instrument includes an interface structure and a shaft connected to the interface structure. The interface structure may be engageable with a drive structure of an actuation interface assembly of a teleoperated surgical system so as to be driven by the drive structure. The shaft is connected to the interface structure and is rotatably driven by the interface structure. The interface structure may comprise a depression shaped and sized to receive a fingertip. The interface structure may comprise one or more gripping features disposed in the depression.

In accordance with another exemplary embodiment, a surgical instrument for a teleoperated surgical system includes an instrument shaft, an end effector coupled to a first end of the shaft, and a force transmission mechanism coupled to a second end of the shaft opposite the first end. The force transmission mechanism may comprise an actuation input mechanism configured to transmit drive forces to actuate the surgical instrument. The actuation input mechanism may comprise an interface structure and an actuation shaft. The interface structure may be engageable with a drive structure of an actuation interface assembly of the teleoperated surgical system so as to be driven by the drive structure. The actuation shaft may be connected to the interface structure. The actuation shaft may be rotatably driven by the interface structure. The interface structure may comprise a depression shaped and sized to receive a fingertip, and wherein the interface structure comprises one or more gripping features disposed in the depression.

In accordance with another exemplary embodiment, a method of cleaning a surgical instrument of a teleoperated surgical system includes positioning a finger-shaped object into a depression of an interface structure of an actuation input mechanism. The depression may be sized and shaped to receive the finger shaped object. The interface structure may be engageable to be driven by a drive structure of an actuation interface assembly of the teleoperated surgical system to actuate one or more components of the surgical instrument. The method may further comprise driving the actuation input mechanism by manipulating the interface structure using the finger-shaped object received in the depression. The method may further comprise actuating one or more components of the surgical instrument in response to the driving for a cleaning procedure.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 18 is a perspective view of an actuation input mechanism, according to another exemplary embodiment.

FIG. 19 is a perspective view of an interface structure, according to an exemplary embodiment.

FIG. 20 is a perspective view of an interface structure in which a second overmolded material has been partially removed to reveal a first material, according to an exemplary embodiment.

DETAILED DESCRIPTION

Figure 1:
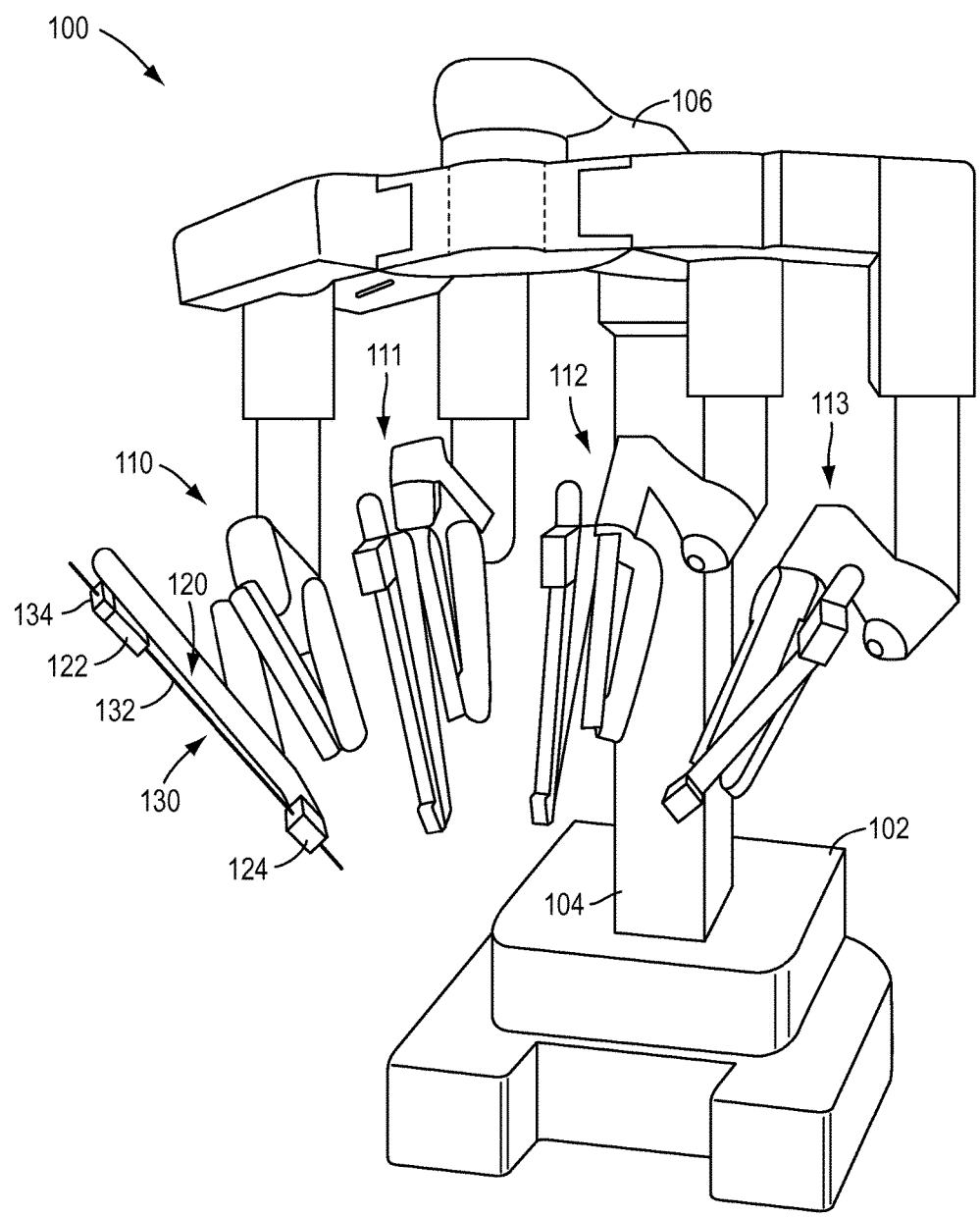
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural references unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates various surgical instrument transmission actuation input mechanisms that include interface structures provided with features to facilitate gripping and manual actuation by a user. For example, features may be provided to assist with a user manually actuating the instrument, such as to facilitate actuation of one or more components of the instrument during a cleaning procedure.

Various exemplary embodiments of the present disclosure contemplate an actuation input mechanism for a surgical instrument that is configured to be driven via engagement with an actuation interface assembly of a patient side cart of a teleoperated surgical system, as well as including features to facilitate being driven via manual manipulation by a user. The actuation input mechanism may comprise an interface structure and an output shaft connected to the interface structure, wherein the output shaft is coupled to various gearing and/or drive members that ultimately couple to and effect motion of various components (e.g., end effector and/or wrist) of the surgical instrument. The interface structure may include at least one depression shaped to receive a fingertip so that the interface structure can be manipulated and moved with the fingertip or other finger-shaped object, such as via rotating a disk-shaped interface structure.

Interface features in accordance with various exemplary embodiments also may include various features to facilitate gripping so that a user's fingertip, or other finger-shaped object, does not slip during manipulation of the interface structure. For example, various gripping features may be located within the depression and/or on other portions of the interface structure that may be available to a user to manipulate in order to manually actuate the actuation interface structure, with the depression including one or more gripping surfaces. The gripping surfaces may include ribs. The ribs may be arranged in a radial pattern extending from a central region of the depression. The ribs may be substantially straight or may be in a spiral pattern. In one example, the ribs may have a profile substantially flush with a surface of the interface assembly the depression is located in. In another example, the ribs have a dished profile relative to a surface of the interface assembly the depression is located in. Tips of the ribs proximate to the central region of the depression may be rounded. The tips may be spaced from a central aperture in the central region. The gripping surfaces may be provided by a single rib having a spiral shape. One or more of the interface structures may have a knurled edge.

In various exemplary embodiments, a force transmission mechanism may be configured to facilitate user access to, and thereby manipulation of, an actuation input mechanism interface structure. For example, a force transmission mechanism housing can include a cutout around an outer periphery to provide access to an edge, which in various exemplary embodiments may be a knurled edge, of an interface structure. The interface structure may be an interface disk. The interface structure may include slots to receive projections of drive structure of an actuation interface assembly of a teleoperated surgical system to actuate the interface structures. The interface structures may comprise a first material and a second material overmolded onto the first material, wherein the second material is more compliant than the first material. Various exemplary embodiments of the present disclosure further contemplate surgical instruments and surgical systems including the actuation input mechanisms of the various exemplary embodiments described herein.

Referring now to FIG. 1, an exemplary embodiment of a patient side cart 100 of a teleoperated surgical system is shown. As those having ordinary skill in the art are familiar with, a teleoperated surgical system may further include a surgeon console (not shown) for receiving input from a user to control instruments mounted at patient side cart 100, as well as an auxiliary control/vision cart (not shown), as described in for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. By way of non-limiting example, a teleoperated surgical system of the type contemplated by the present disclosure includes a da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif.

Patient side cart 100 includes a base 102, a main column 104, and a main boom 106 connected to main column 104. Patient side cart 100 also includes a plurality of manipulator arms 110, 111, 112, 113, which are connected to main boom 106. Portions of manipulator arms 110, 111, 112, 113 include an instrument mount portion 120 to which an instrument 130 may be mounted, as illustrated for manipulator arm 110. Manipulator arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 includes an actuation interface assembly 122 and an accessory mount 124. According to various exemplary embodiments, a shaft 132 of instrument 130 can extend through accessory mount 124 (and on to a surgery site during a surgical procedure) and a force transmission mechanism 134 of instrument can connect with the actuation interface assembly 122. Accessory mount 124 is configured to hold a cannula (not shown) through which shaft 132 of instrument 130 may extend to a surgery site during a surgical procedure. Actuation interface assembly 122 includes a variety of mechanisms that are controlled to respond to input commands at the surgeon console and transmit forces to the force transmission mechanism 134 to actuate instrument 130.

Although the exemplary embodiment of FIG. 1 shows an instrument 130 attached to only manipulator arm 110 for ease of illustration, those having ordinary skill in the art would appreciate that an instrument may be attached to any and each of manipulator arms 110, 111, 112, 113. A surgical instrument 130, as contemplated herein, may be an instrument with an end effector or may be a camera instrument or other sensing instrument utilized during a surgical procedure to provide information, (e.g., visualization, electrophysiological activity, pressure, fluid flow, and/or other sensed data) of a remote surgical site. In the exemplary embodiment of FIG. 1, either an instrument with an end effector or a camera instrument may be attached to and used with any of manipulator arms 110, 111, 112, 113. However, the embodiments described herein are not limited to the exemplary embodiment of FIG. 1 and various other teleoperated surgical system configurations may be used with the exemplary embodiments described herein.

Figure 2:
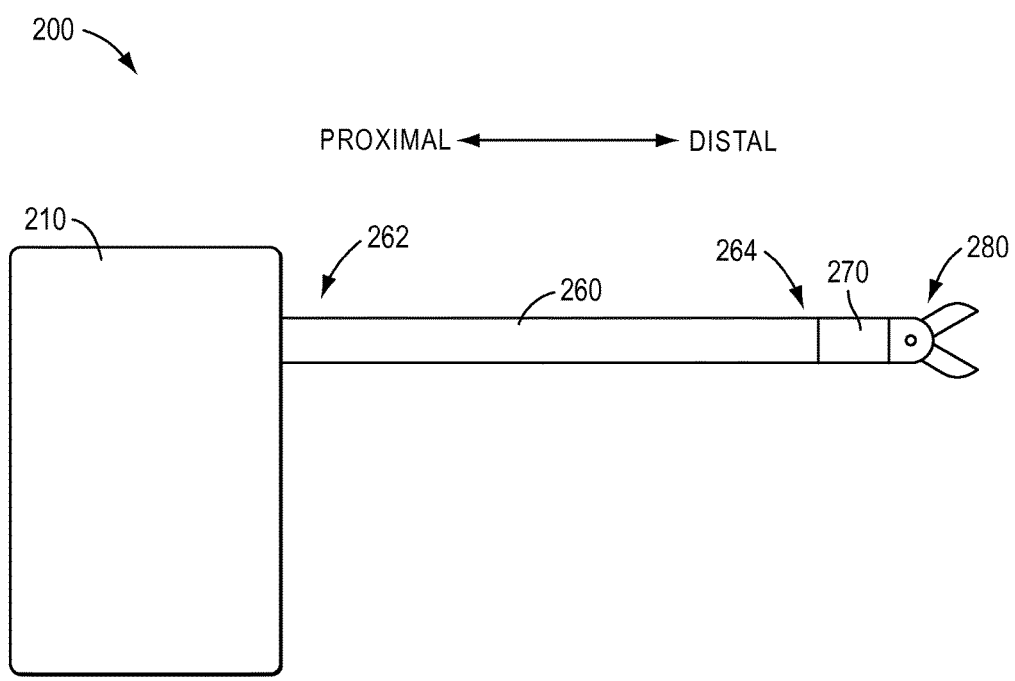
FIG. 2 is a schematic side view of a surgical instrument, according to an exemplary embodiment.

Turning to FIG. 2, an exemplary embodiment of a surgical instrument 200 with an end effector 280 at a distal end 264 of shaft 260 is shown. Surgical instrument 200 further includes a force transmission mechanism 210 connected to shaft 260. According to an exemplary embodiment, surgical instrument 200 may optionally include a wrist 270 to move end effector 280 in arbitrary pitch and/or yaw directions relative to shaft 260. According to another exemplary embodiment, surgical instrument 200 may be a non-wristed instrument and thus lack wrist 270. Surgical instrument 200 may include one or more members to translate force between force transmission mechanism 210 and end effector 280 and/or wrist 270 to actuate end effector 280 and/or wrist 270. For instance, one or more drive member(s) (not shown) may connect force transmission mechanism 210 to end effector 280 and/or wrist 270 to provide actuation forces to end effector 280 and/or wrist 270, such as by extending along an interior of shaft 260 from transmission mechanism 210. Drive member(s) may include, for example, push/pull drive members (e.g., rod), pull/pull drive members (e.g., wires and cables), rotary members (e.g. drive shafts), and other drive members familiar to one of ordinary skill in the art.

Force transmission mechanism 210 includes one or more components to engage with a patient side cart of a teleoperated surgical system to translate a force provided by patient side cart to surgical instrument 200. For instance, force transmission mechanism 210 may engage with actuation interface assembly 122 in the exemplary embodiment of FIG. 1 (as force transmission mechanism 134 engages actuation interface assembly 122 in FIG. 1) to receive input forces transmitted from actuation interface assembly 122 to actuate instrument 200, such as to actuate end effector 280 and/or wrist 270.

Figure 3:
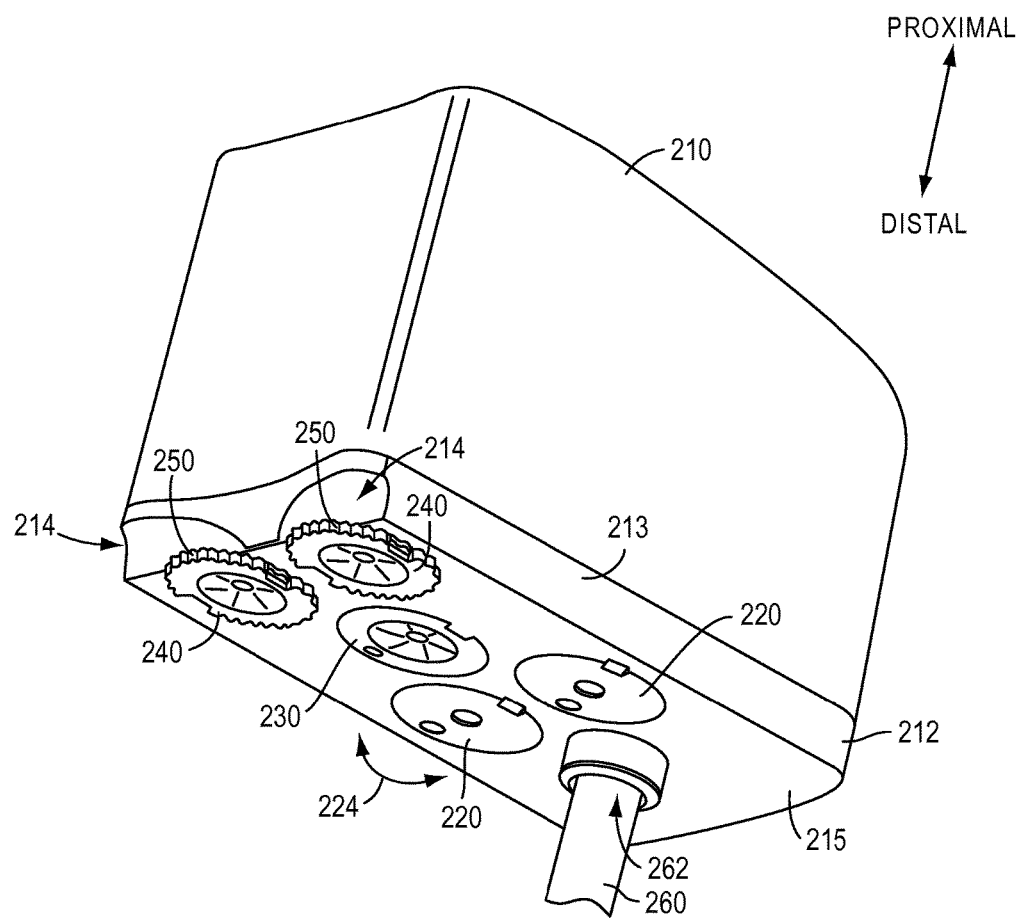
FIG. 3 is a partial perspective view of the surgical instrument of FIG. 2.

Turning to FIG. 3, a partial perspective view is shown of the force transmission mechanism 210 and shaft 260 of the instrument 200 of FIG. 2. As shown in FIG. 3, force transmission mechanism 210 includes a chassis 212 through which a proximal end 262 of shaft 260 extends into force transmission mechanism 210. According to an exemplary embodiment, chassis 212 may be made of a molded plastic, such as, for example, a polyetherimide or other plastic familiar to one of ordinary skill in the art. Force transmission mechanism 210 also may include a plurality of actuation input mechanisms to receive a force to actuate instrument 200. As shown in FIG. 3, the actuation input mechanisms include interface disks 220, 230, and 240 that engage with drive structures of an actuation interface assembly of a patient side cart, such as the actuation interface assembly 122 of the patient side cart 100 of the exemplary embodiment of FIG. 1. As will be described in more detail below, the actuation input mechanisms may be connected to cable(s), gearing, or other structures (e.g., within force transmission mechanism 210) to transmit forces applied to interface disks 220, 230, 240 and actuate a functionality of instrument 200 associated with interface disks 220, 230, 240. Thus, interface disks 220, 230, and 240 utilize actuation forces from an actuation interface assembly to actuate instrument 200.

Figure 4:
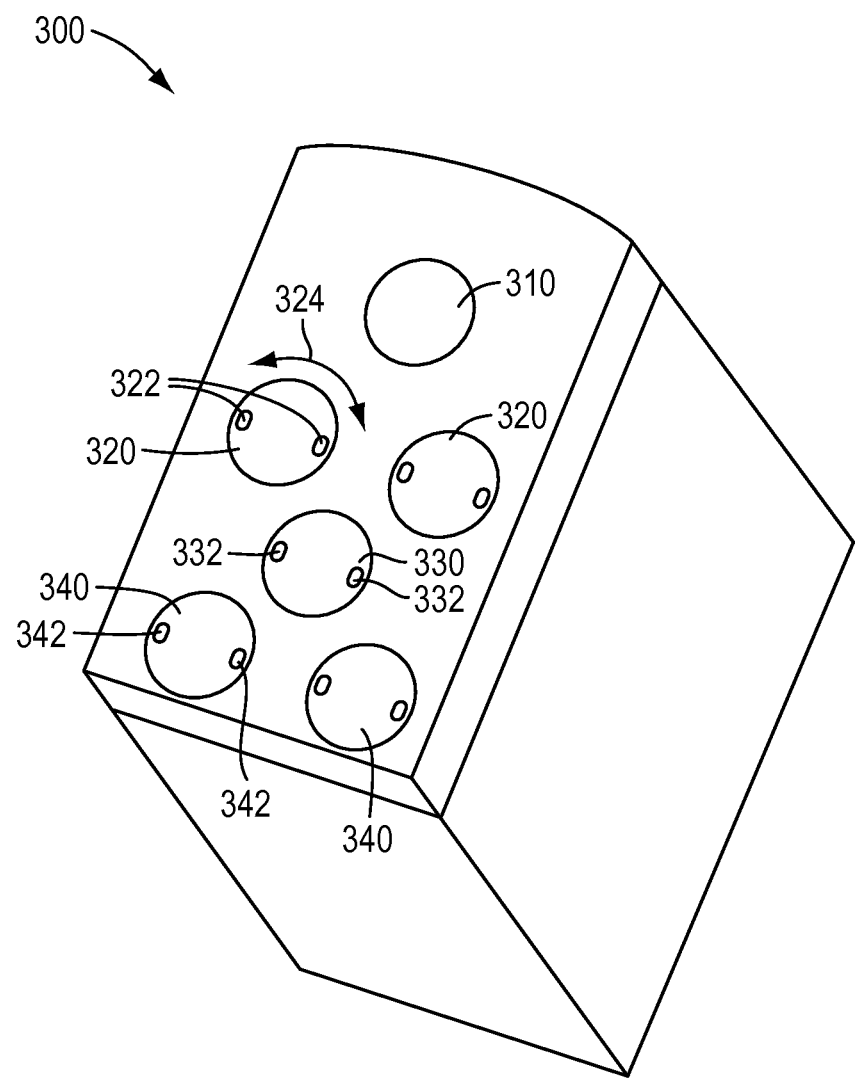
FIG. 4 is a partial perspective view of an actuation interface assembly, according to an exemplary embodiment.

Turning to FIG. 4, an exemplary embodiment of an actuation interface assembly 300 is shown. Actuation interface assembly 300 may be used as actuation interface assembly 122 in FIG. 1 to engage with a surgical instrument force transmission mechanism, such as with force transmission mechanism 134 or 210. Actuation interface assembly 300 includes an aperture 310 into which a shaft of an instrument (e.g., shaft 260 in FIG. 3) can be inserted so the instrument shaft extends from the actuation interface assembly 300 to a surgical site (not shown). Actuation interface assembly 300 further includes drive structures to transmit a force to actuation input mechanisms of a surgical instrument force transmission mechanism. As shown in the exemplary embodiment of FIG. 4, actuation interface assembly 300 can include drive disks 320, 330, and 340 to respectively engage with interface disks 220, 230, and 240 of force transmission mechanism 210 when force transmission mechanism 210 is engaged with actuation interface assembly 300.

According to an exemplary embodiment, actuation interface assembly 300 also may include one or more motors (not shown) to rotate drive disks 320, such as in directions 324 in FIG. 4, although a force to rotate drive disk 320 may be supplied by other means, such as motors onboard the transmission mechanism of the instrument and not located within actuation interface assembly 300. When drive disk 320 engages a corresponding interface disk 220 of force transmission mechanism 210, the interface disk 220 can be rotated in directions 224 to operatively actuate the functionality associated with interface disk 220. Similarly, other drive disks 320, 330, and 340 may be rotated in directions 324 to drive corresponding interface disks 220, 230, and 240 of force transmission mechanism 210. Thus, drive disks 320, 330, and 340 may engage with interface disks 220, 230, and 240, to impart a force to rotate and drive interface disks 220, 230, and 240, which in turn actuate instrument 200 via associated actuation input mechanisms.

Figure 5:
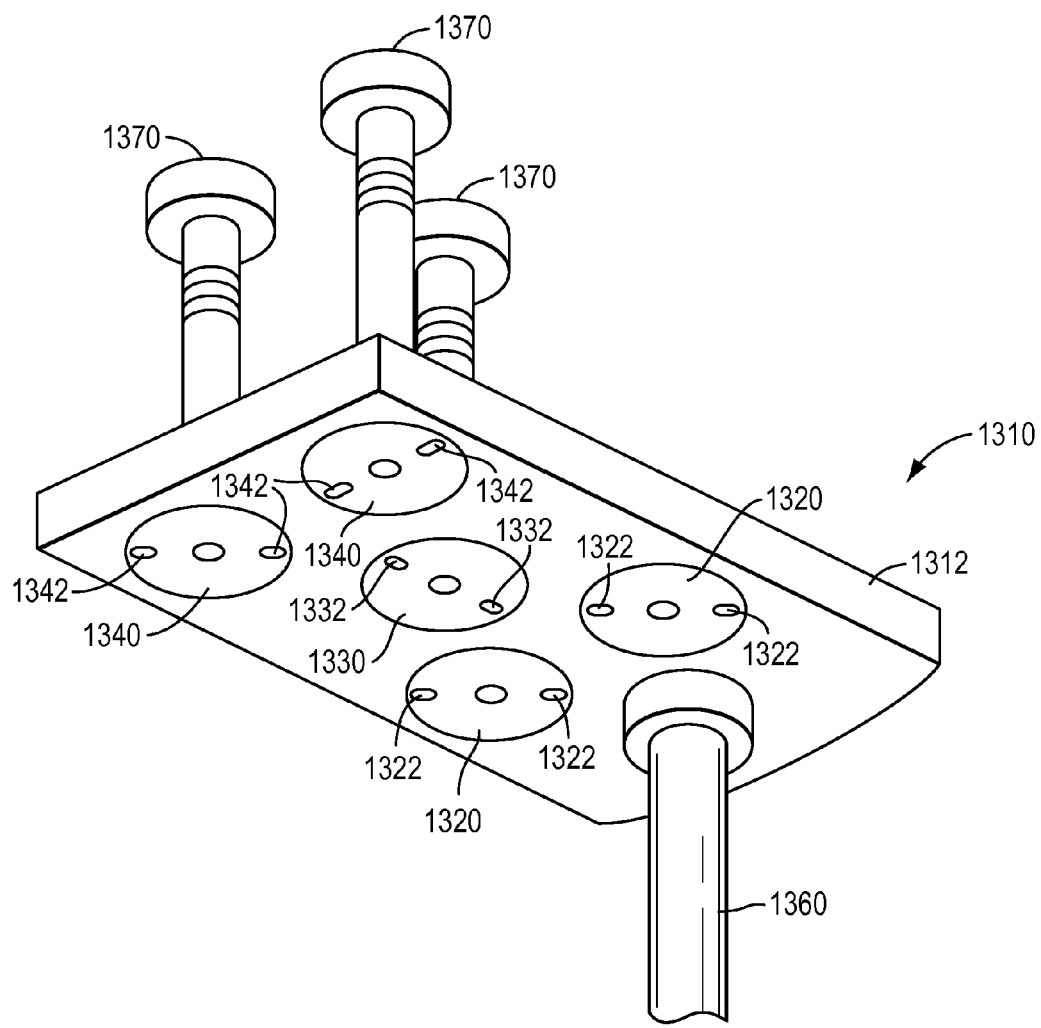
FIG. 5 is a partial perspective schematic view of a surgical instrument with the transmission mechanism housing removed to reveal some internal components thereof, according to an exemplary embodiment.

FIG. 5 shows some internal components of a force transmission mechanism 1310 that includes a chassis 1312 to which a shaft 1360 of a surgical instrument is connected, as discussed above with regard to the exemplary embodiment of FIG. 3. Force transmission mechanism 1310 also includes the interface disks 1320, 1330, 1340 of actuation input mechanisms 1370. Interface disks 1320, 1330, 1340 may be configured according to the various exemplary embodiments of interface disks described herein. For example, interface disks 1320, 1330, 1340 may respectively include slots 1322, 1332, 1342 to engage with projections 322, 332, 342 of drive disks 320, 330, 340 of the actuation interface assembly 300 of the exemplary embodiment of FIG. 4 to receive a force from drive disks 320, 330, 340 and actuate functionalities associated with interface disks 1320, 1330, 1340, as will be discussed below.

Figure 6:
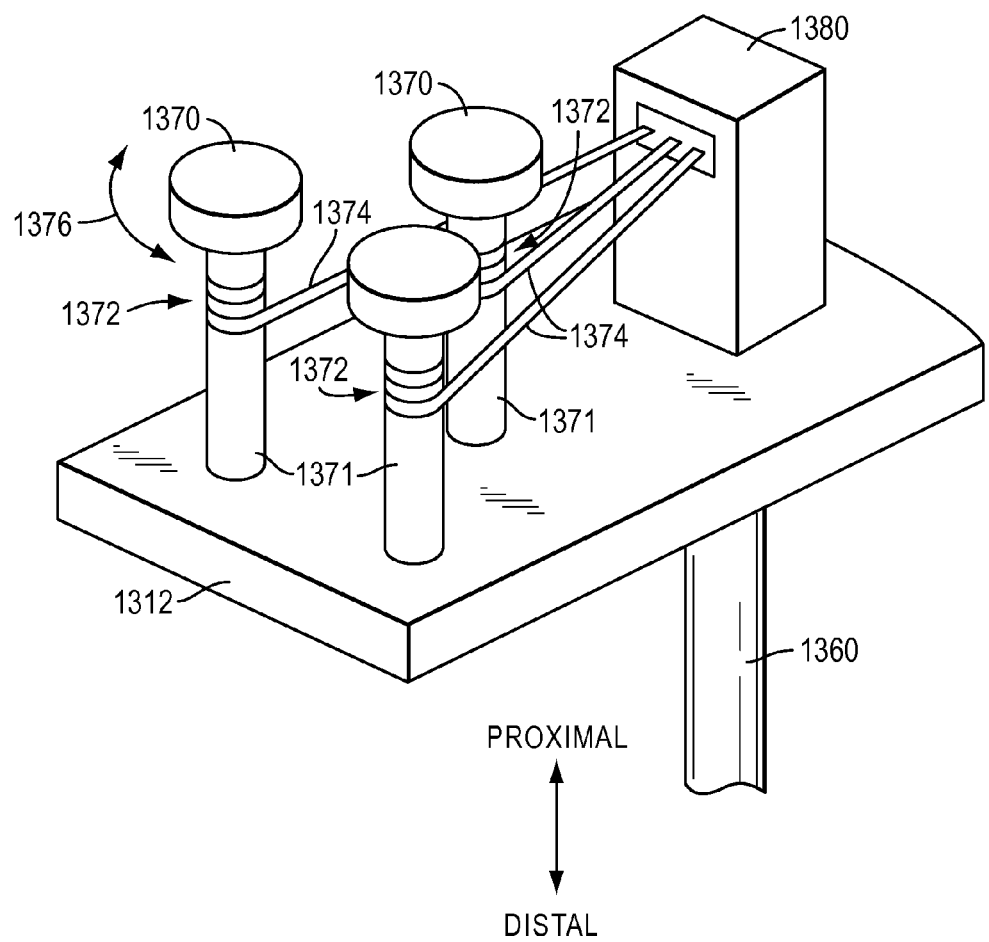
FIG. 6 is a partial perspective schematic view of a surgical instrument similar to FIG. 5 with some internal components revealed, according to an exemplary embodiment.

As shown in FIGS. 5 and 6, one or more of interface disks 1320, 1330, 1340 may be part of actuation input mechanisms 1370. Although FIGS. 5 and 6 show that only interface disks 1330 and 1340 are part of actuation input mechanisms 1370 (with interface disks 1320 being connected to other actuation mechanisms), more or fewer of interface disks 1320, 1330, 1340 may be part of actuation input mechanisms 1370. Actuation input mechanisms 1370 may include an interface disk (e.g., interface disk 1320, 1330, or 1340) at one end, as shown in FIGS. 5 and 6, and an output shaft 1371. In various exemplary embodiments, the output shaft is provided with an output section 1372 (see FIG. 6) configured to couple the shaft 1371 to other components of the surgical instrument so as to enable actuation of those components in response to rotation of the output shaft 1371. Output section 1372 may include, for example, gear teeth, a rack, screw threads, grooves, or other structures to interact with other mechanisms and output forces applied to actuation input mechanism 1370 to in turn actuate one or more components of the surgical instrument. A drive member or the surgical instrument may be connected to output section 1372 in this manner.

For example, in the exemplary embodiment of FIG. 6, cables 1374 are connected to the output sections 1372 (which may be, for example, grooves or threads in shaft 1371 to receive a cable 1374) of actuation input mechanism 1370. Thus, when an actuation input mechanism 1370 is rotated in directions 1376 (e.g., due to a force applied to an interface disk of actuation input mechanism 1370), cable 1374 is paid out or wound upon output section 1372, causing a component of the surgical instrument associated with the cable 1374 and the actuation input mechanism 1370 to be actuated. As shown in the exemplary embodiment of FIG. 6, the cables 1374 connected to actuation input mechanisms 1370 may be connected to a mechanism 1380 at a proximal portion of instrument shaft 1360 to allow the cables 1374 to ultimately connect to and actuate various components (e.g., to achieve various functionalities) associated with the surgical instrument.

The component functionalities associated with interface disks 220, 230, and 240 (and interface disks 1320, 1330, 1340) and their corresponding actuation input mechanisms may be selected from amongst, for example, actuating end effector 280 of instrument 200 of FIG. 2 (e.g., opening and/or closing end effector 280), moving wrist 270 in an arbitrary yaw direction, moving wrist 270 in an arbitrary pitch direction, rolling shaft 260 (as well as end effector 280), and other functionalities familiar to one of ordinary skill in the art. Further, although five interface disks and five corresponding drive disks are shown in the exemplary embodiments of FIGS. 3-6, force transmission mechanisms and actuation interface assemblies of the various exemplary embodiments described herein may include other numbers of respective disks, such as, for example, two, three, four, six, or more disks. Moreover, those having ordinary skill in the art would appreciate that a single actuation input mechanism can actuate more than one component and/or component functionality in accordance with various exemplary embodiments, based on, for example, the gearing, drive members, etc. to which the output shaft may be coupled.

Figure 7:
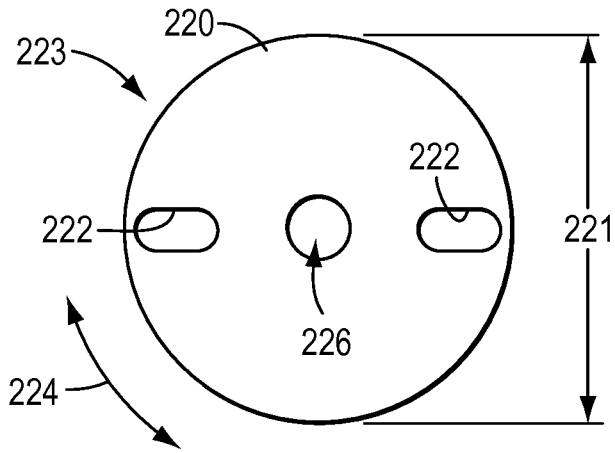
FIG. 7 is a plan view of an actuation input mechanism, according to an exemplary embodiment.

Drive disks 320, 330, and 340 and interface disks 220, 230, and 240 may include structures to facilitate engagement and the transfer of forces between the disks. As shown in the exemplary embodiment of FIG. 4, drive disks 320 includes projections 322 to engage with corresponding structures of an interface disk. According to an exemplary embodiment, interface disk 220 includes slots 222 to receive projections 322 of drive disk 320, as shown in FIG. 7, which depicts an end view of drive disk 320. Slots 222 have a shape corresponding to a shape of projection 322. Thus, when a drive disk 320 is rotated in directions 324 in FIG. 4, projections 322 inserted within slots 222 may in turn facilitate driving interface disk 220 in directions 224, as shown in FIG. 7. The present disclosure contemplates that the interface disk, drive disk, and an intermediate disk of a sterile adapter are configured to provide an Oldham coupling, with the projections of the drive disk being able to slide radially within the grooves. Although FIGS. 4 and 7 depict projections 322 on drive disk 320 and slots 222 on interface disk 220, the location of these structures may be reversed, with slots on drive disk 320 and projections on interface disk 220. Further, the number, position, shape, and other features of projections 322 and slots 222 may be modified relative to the exemplary embodiments depicted in FIGS. 4 and 7. Drive disks 330, 340 and interface disks 230, 240 may be structured in a similar manner and respectively include projections 332, 342 to facilitate engagement and transfer of forces between the disks. In various exemplary embodiments, interface disks 220, 230, and 240 may be made of a molded plastic, such as, for example, a polyetherimide or other plastic familiar to one of ordinary skill in the art. Further, interface disk 220 may have an outer diameter 221 in FIG. 7 ranging from, for example, about 0.50 inches to about 1.00 inches. Interface disks 230 and 240 may have the same outer diameter as interface disk 220.

Interface disks of a force transmission mechanism may be structured and positioned to protect the interface disks from damage. For example, as shown in the exemplary embodiment of FIG. 3, interface disks 220, 230, and 240 are located within recesses of chassis 212 to minimize the amount of surface area of interface disks 220, 230, and 240 that is exposed and could be subjected to an impact or other potentially damaging event. For example, the exposed surfaces of interface disks (e.g., interface disks 220, 230, and/or 240) of force transmission mechanism 200 in FIG. 3 may be substantially level with a surface 215 of chassis and an edge 213 of chassis may surround the interface disks to provide a degree of protection to the interface disks.

As discussed above, it may be desirable to actuate an instrument during a cleaning procedure, such as, for example, to actuate an end effector and/or wrist of the instrument to facilitate cleaning. To actuate the instrument component(s) during such a cleaning procedure, it may be desirable for a user to manually drive the interface disks, and thereby corresponding actuation input mechanisms, of the force transmission mechanism of the instrument instead of, for example, gripping the component directly to manually move and/or actuate it. Thus, it may be desirable to arrange and configure actuation input mechanisms, including interface structures, to facilitate gripping and manipulation of the same, for example, permitting a user's fingers, or other finger-shaped object, to manipulate the actuation input mechanism and manually actuate an instrument during a cleaning procedure.

Although all interface disks of a force transmission mechanism could include gripping features according to the various exemplary embodiments described herein, not all interface disks need to include such gripping features. For example, interface disks 220 of FIGS. 3 and 7 may be associated with an actuation input mechanism used to actuate a functionality of an instrument that is not needed during a cleaning operation, such as, for example, rolling a shaft of an instrument. Because a user is unlikely to manually actuate interface disks 220 during a cleaning procedure, interface disks 220 need not include gripping features and/or other features to facilitate manual manipulation of disks 220 described herein, although disks 220 could include such gripping features and/or other features.

Figure 8:
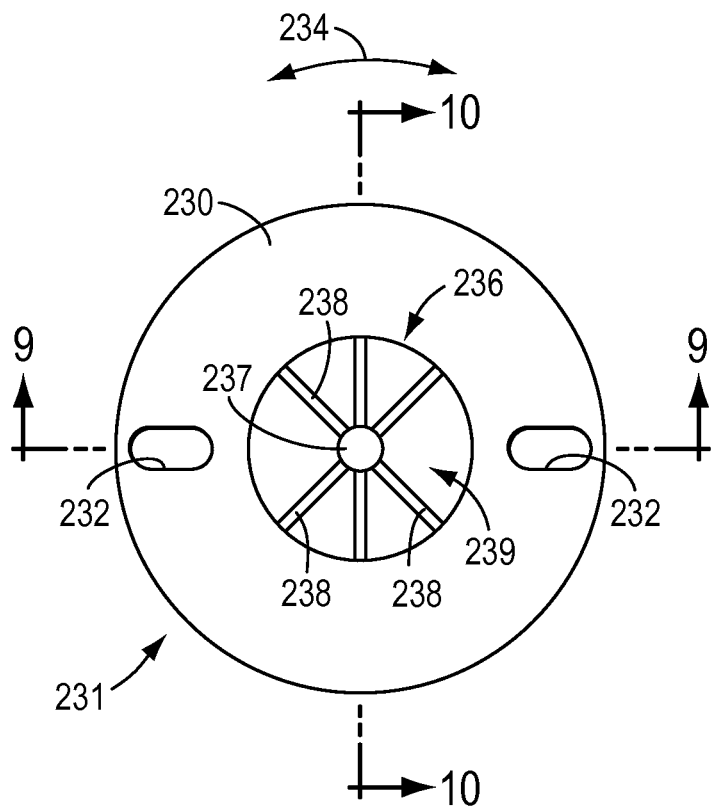
FIG. 8 is a plan view of an actuation input mechanism, according to another exemplary embodiment.
Figure 9:
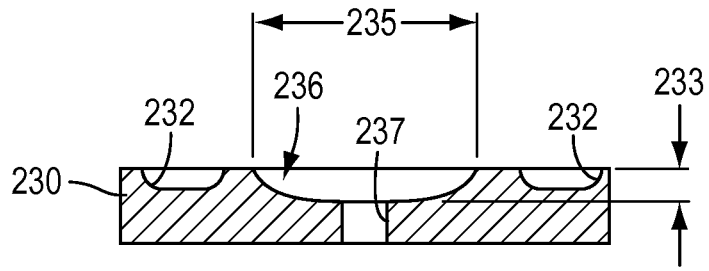
FIG. 9 is a cross-sectional view along line 9-9 of FIG. 8.

Turning to FIG. 8, an end view is shown of interface disk 230 of force transmission mechanism 210 of FIG. 3. As shown in FIG. 8, interface disk 230 includes slots 232 to receive projections 332 of drive disk 330, similar to the configuration described with reference to FIG. 7, and a central aperture 237. According to an exemplary embodiment, central aperture 237 may be used, for example, as an aid during assembly of force transmission mechanism 210. For instance, central aperture 237 may vary in size and/or depth from one interface disk to another so that the various interface disks may be distinguished from one another to facilitate correct placement of the interface disks in force transmission mechanism 210. According to an exemplary embodiment, central aperture 237 may be used, for example, as an aid during molding of an interface disk, such as to facilitate positioning of a part within a mold, such as a shaft (not shown) being overmolded with plastic. Interface disk 230 further includes a depression 236 that serves as a gripping feature. According to an exemplary embodiment, depression 236 may be shaped to receive a fingertip of a user or a finger-shaped object, such as, for example, a stylus, pencil, or other specially-designed tool having a configuration similar to a finger. As shown in FIG. 9, which is a cross-sectional view of FIG. 8 along line 9-9, depression 236 can have various dimensions for its depth, radius of curvature and diameter. For example, the depth of the depression 233 may range from about 0.010 inches to about 0.050 inches. The radius of curvature may range from about 0.032 inches to about 2.000 inches, for example. The diameter 235 may range from about 0.600 inches to about 0.1875 inches, for example.

Figure 10:
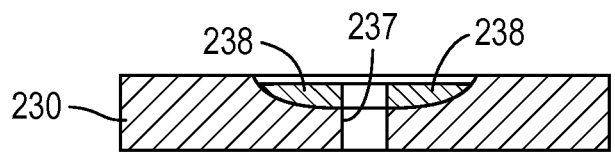
FIG. 10 is a cross-sectional view along line 10-10 of FIG. 8.

Depression 236 may include gripping structures to facilitate gripping of interface disk via a fingertip inserted into depression 236. Depression 236 may also be gripped by a finger-shaped object, such as, for example, a stylus, pencil, or other specially-designed tool having a configuration similar to a finger. According to an exemplary embodiment, interface disk 230 includes a plurality of ribs 238 located within depression 236, as shown in FIG. 8 and FIG. 10, which is a cross-sectional view along line 10-10 of FIG. 8. Thus, when a user inserts a fingertip or a finger-shaped object into depression 236, ribs 238 engage the fingertip or the finger-shaped object to facilitate gripping interface disk 230. Further, the fingertip of the user or the object may be pressed into spaces 239 of depression 236 between ribs 238 when the fingertip is pressed against ribs 238, which may enhance gripping of interface disk 230. Furthermore, the user's fingernail can be projected into the spaces between the ribs 238 so as to engage against the sides of the ribs for better traction. Similarly, a tool, such as, for example, a flat-bladed screwdriver, may be used to rotate the input. To minimize or prevent damage to a fingertip or a glove worn on the hand of a user, edges of ribs 238 may be rounded to reduce the sharpness of the edges.

As shown in the exemplary embodiment of FIG. 8, ribs 236 have a radial arrangement, with ribs 236 extending along straight radial lines in relation to aperture 237, although the various interface disk embodiments described herein may use other rib arrangements. In addition, although the exemplary embodiment of FIG. 8 depicts an interface disk with six ribs 238, the interface disks of the various exemplary embodiments described herein may include other numbers of ribs, such as, for example, three ribs, four ribs, five ribs, seven ribs, eights ribs, or more ribs. Further, although various exemplary embodiments of interface disks described herein may include ribs, such as ribs 238 in FIG. 8, a depression (e.g., depression 236 in FIG. 8) may include other structures to facilitate gripping of a fingertip or a finger-shaped object inserted into the depression, such as, for example, a plurality of bumps, a roughened surface of the depression, or other structures familiar to one of ordinary skill in the art.

Figure 11:
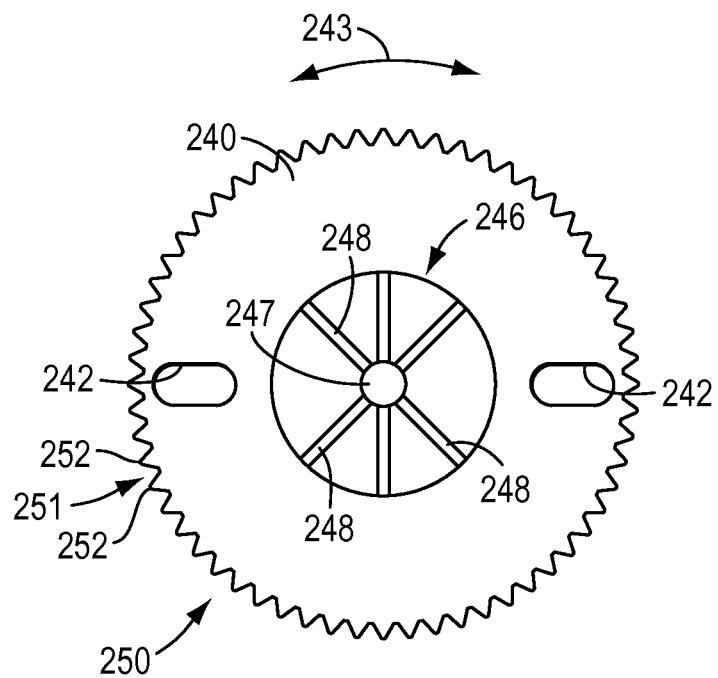
FIG. 11 is a plan view of an actuation input mechanism, according to another exemplary embodiment.

An interface disk of a force transmission mechanism may include other gripping structures than a depression and gripping structures inside the depression. Turning to FIG. 11, an end view is shown of interface disk 240 of force transmission mechanism 210 of FIG. 3. As shown in FIG. 11, interface disk 240 may include slots 242 to receive projections 342 of a drive disk 340, a central aperture 247, and a depression 246. Depression 246 may be structured in the same way as depression 236 of interface disk 230 of the exemplary embodiment of FIGS. 8-10. For instance, depression 236 may include gripping structures, such as ribs 248. According to an exemplary embodiment, interface disk 240 also includes a knurled edge 250 as a gripping structure in addition to depression 246 and any gripping structures of depression (e.g., ribs 248). Knurled edge 250 may include, for example, peaks 252 separated by grooves 251, as shown in FIG. 11, so that knurled edge 250 provides a feature that facilitates gripping by a user's hand. Thus, an interface disk may include either a depression with its gripping structures or a knurled edge, or include both the depression with its gripping structures and a knurled edge.

Knurled edge 250 is configured to be gripped by a user pressing a fingertip or finger-shaped object against knurled edge 250 to rotate interface disk 240 in directions 243 in FIG. 11. As discussed above with regard to FIG. 3, interface disks 220, 230, 240 may be recessed within chassis 212 to provide a degree of protection to the interface disks, according to an exemplary embodiment. Because such an arrangement in which interface disks are recessed may interfere with a user's ability to access an edge of the interface disks, a force transmission mechanism 210 may include structures to facilitate access to an edge of an interface disk. For example, the chassis including the interface disks may include a cutout to facilitate access to an edge of one or more of the interface disks. As shown in the exemplary embodiment of FIG. 3, edge 213 of chassis 212 may include cutouts 214 so that knurled edges 250 of interface disks 240 may be easily accessed by a user, such as to manually turn interface disks 240 during a cleaning procedure. According to an exemplary embodiment, cutouts 214 may be provided for interface disks that actuate a functionality of instrument 200 a user may utilize during a cleaning operation, such as, for example, opening or cleaning end effector 280, while cutouts 214 are not provided for other interface disks. Thus, cutouts may be provided on interface disks 240 and not on interface disks 220 and 230, according to an exemplary embodiment. As shown in FIGS. 7 and 8, interface disks 220 and 230 may have respective edges 223 and 231 that lack a knurled edge since those disks 220 are used to actuate a functionality of an instrument that is not needed during a cleaning operation, such as, for example, rolling a shaft of an instrument, and/or are not be located proximate to edge 213 of chassis 212.

According to another exemplary embodiment, all interface disks may include a knurled edge (e.g., knurled edge 250 of FIG. 11). Thus, interface disks 220 and 230 are not limited to lacking knurled edges but instead may have knurled edges to facilitate gripping their edges and their manual actuation. Further, cutouts may be provided for all interface disks of a force transmission mechanism, such as when all interface disks 220, 230, and 240 have a knurled edge. For instance, cutouts 214 may be provided for interface disks proximate to chassis edge 213 (e.g., interface disks 220 and 240), and a cutout (not shown) may be provided in surface 215 of chassis 212 to provide access to a knurled edge of interface disk 230.

Figure 12:
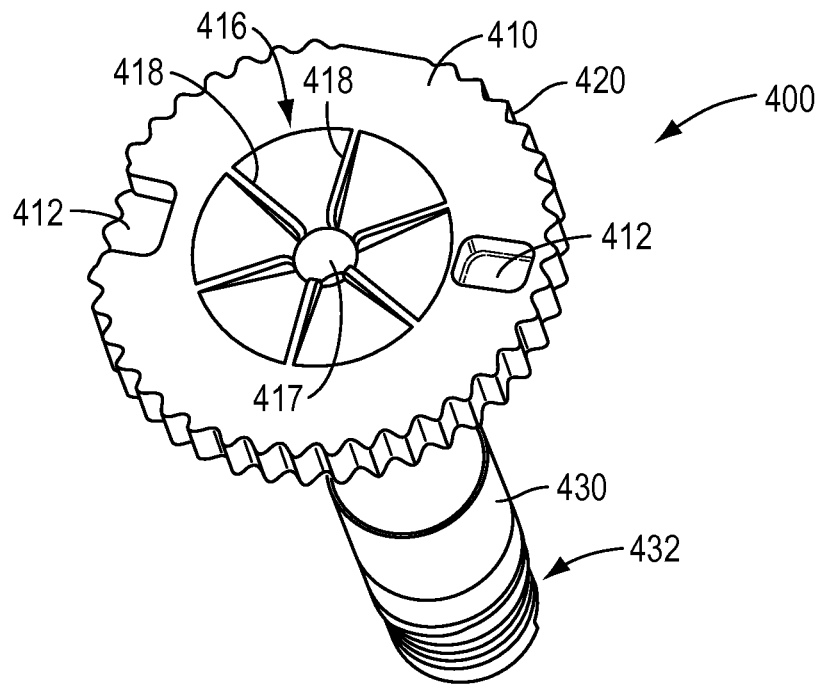
FIG. 12 is a perspective view of an actuation input mechanism, according to an exemplary embodiment.

As discussed above with regard to FIGS. 8-11, a depression of an interface disk may include gripping structures, such as ribs arranged in the radial pattern shown in the exemplary embodiments of FIGS. 8-11. Turning to FIG. 12, an exemplary embodiment is shown of an actuation input mechanism 400 for a force transmission mechanism, such as force transmission mechanism 210 of FIGS. 2 and 3. Actuation input mechanism 400 includes an interface disk 410 and shaft 430 joined to interface disk 410. A plurality of actuation input mechanisms may be arranged according to the positions of interface disks illustrated in the exemplary embodiment of FIGS. 3 and 8-11. Interface disk 410 also includes slots 412, a central aperture 417, a depression 416 with gripping structures, such as, for example, ribs 418 in the radial pattern shown in FIG. 12, and a knurled edge 420. Thus, interface disk 410 is configured to be actuated by projections (not shown) of a drive disk (such as projections 322 of drive disk 320 in the exemplary embodiment of FIG. 4) or by a user engaging depression 416 or knurled edge 420 to turn interface disk 410. Because shaft 430 is joined to interface disk 410 (e.g., as a single piece or as separate pieces joined to one another), shaft 430 rotates as well. Shaft 430 may include an output section 432, which may be connected to cables, gearing, or other structures to actuate one or more components and/or component functionalities of an instrument.

Figure 13:
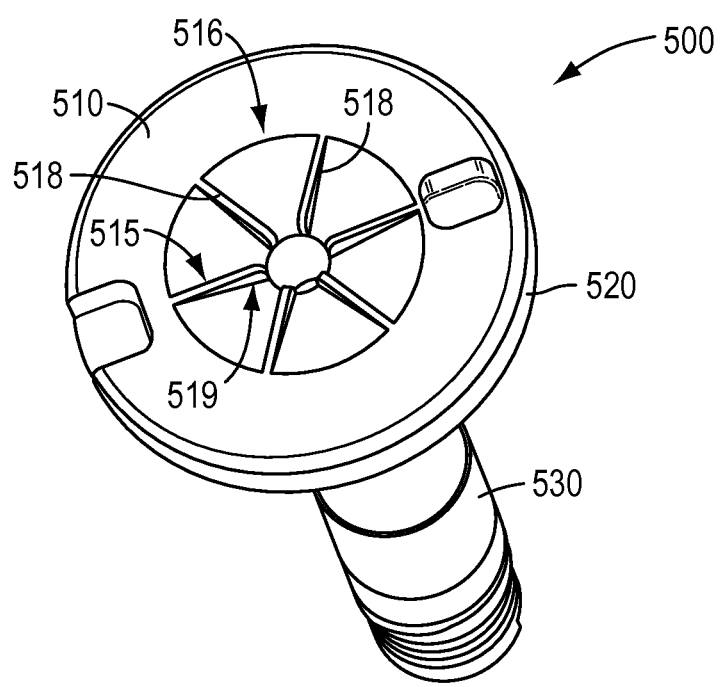
FIG. 13 is a perspective view of an actuation input mechanism, according to another exemplary embodiment.
Figure 14:
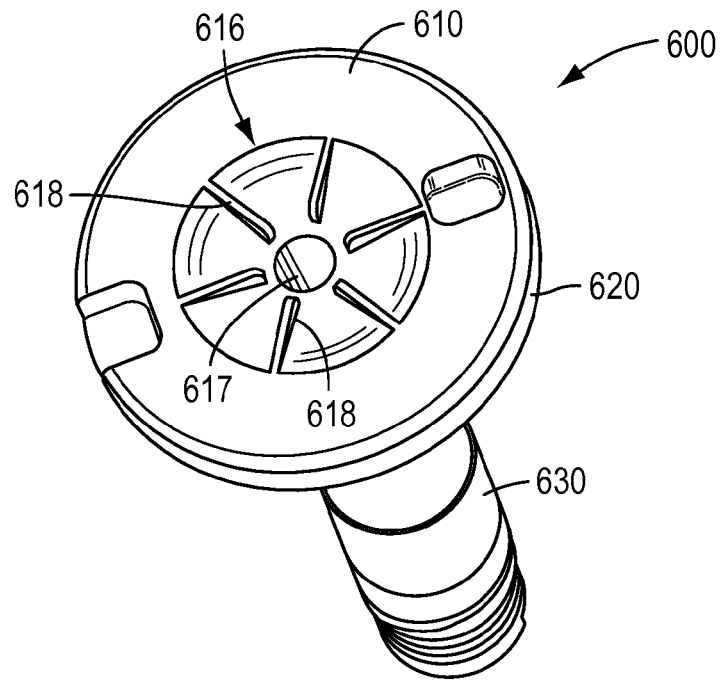
FIG. 14 is a perspective view of an actuation input mechanism, according to another exemplary embodiment.

The depressions of interface disks of the various exemplary embodiments described herein, however, are not limited to the arrangements shown in FIGS. 8-12. Instead, other rib arrangements and structures may be used to facilitate gripping a depression of an interface disk. Turning to FIG. 13, an actuation input mechanism 500 is shown that includes an interface disk 510 and shaft 530. Interface disk 510 and shaft 530 can be arranged according to the exemplary embodiment of FIG. 12, except that ribs 518 of depression 516 may include rounded edges, according to an exemplary embodiment. For example, edges 515 along the length of ribs 518 may be rounded or tips 519 of ribs 518 may be rounded, or both edges 515 and tips 519 of ribs 518 may be rounded. Although edge 520 of interface disk 510 may lack a knurled edge, as shown in FIG. 13, edge 520 may instead be knurled, as shown in FIGS. 11 and 12. According to another exemplary embodiment shown in FIG. 14, an actuation input mechanism 600 may include an interface disk 610 and a shaft 630, which may be arranged according to the exemplary embodiment of FIG. 12, except that ends of ribs 618 in depression 616 may be spaced from a central aperture 617. Spacing ribs 618 from central aperture 617 may assist with, for example, molding input member 600. Although edge 620 of interface disk 610 may lack a knurled edge, as shown in FIG. 14, edge 620 may instead be knurled, as shown in FIGS. 11 and 12.

Figure 15:
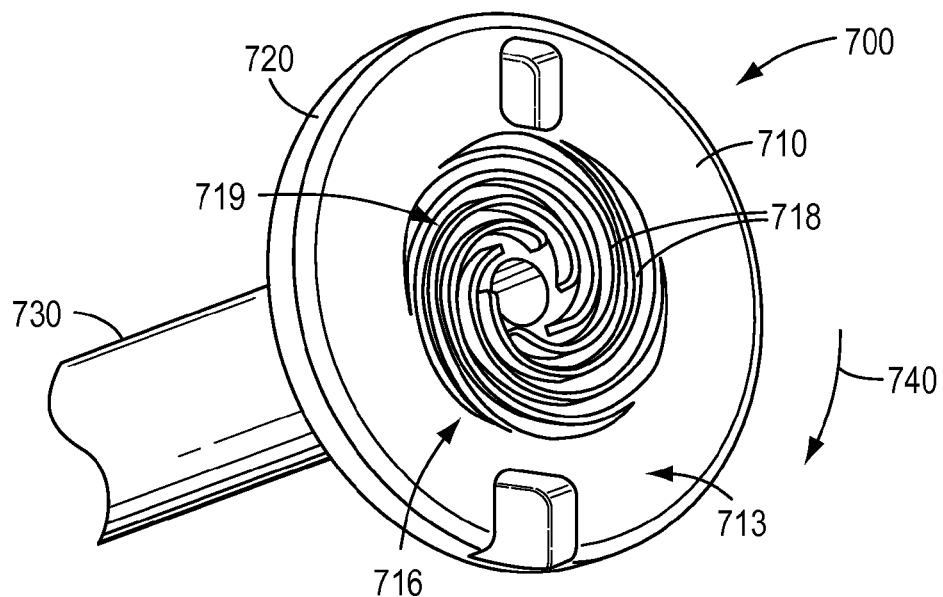
FIG. 15 is a perspective view of an actuation input mechanism, according to yet another exemplary embodiment.

The depressions of interface disks of the various exemplary embodiments described herein are not limited to the radially patterned ribs shown in the exemplary embodiments described above and instead may include other arrangements. FIG. 15 shows an exemplary embodiment of an actuation input mechanism 700 that includes an interface disk 710 and a shaft 730, which may be arranged according to the exemplary embodiment of FIG. 12, except that ribs 718 of depression 716 have a partial spiral shape. As a result, when a user engages depression 716, such as by inserting a fingertip or a finger-shaped object within depression 716, turning of interface disk 710 in direction 740 in FIG. 15 is facilitated because the fingertip or object will wedge between ribs 718 when the fingertip, or finger-shaped object, and interface disk 710 are turned in direction 740. According to an exemplary embodiment, ribs 718 may spiral along a constant radius of curvature. According to another exemplary embodiment, ribs 718 may spiral along a radius of curvature that varies. Although edge 720 of interface disk 710 may lack a knurled edge, as shown in FIG. 15, edge 720 may instead be knurled, as shown in FIGS. 11 and 12.

Figure 16:
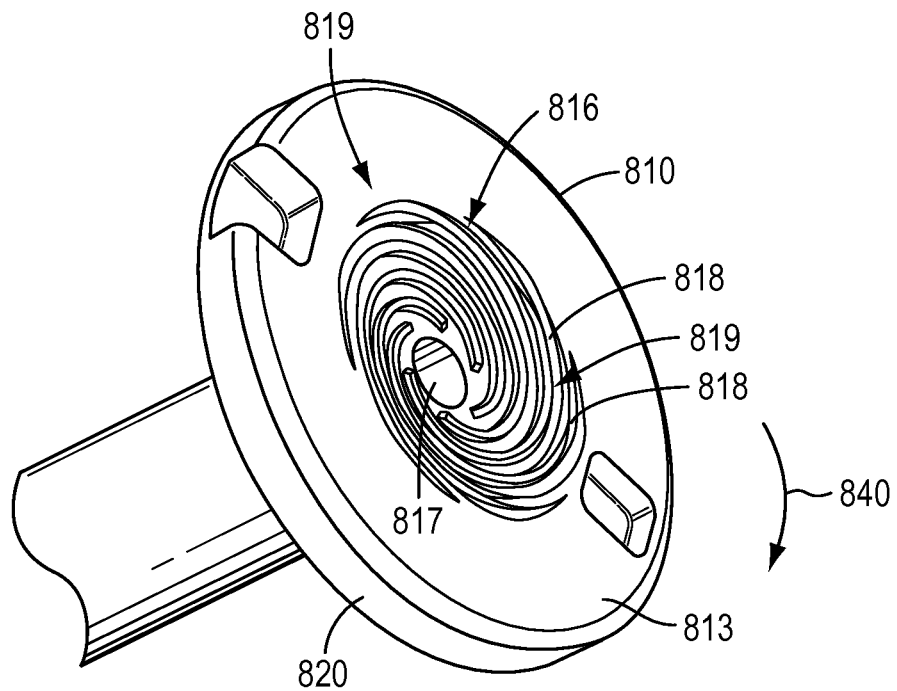
FIG. 16 is a perspective view of an actuation input mechanism, according to another exemplary embodiment.

In the exemplary embodiment of FIG. 15, top surfaces 719 of ribs 718 are substantially flush with a surface 713 of interface disk 710. Thus, ribs 718 have a profile substantially flush with surface 713, and surfaces 719 and 713 may be substantially planar. However, ribs may have a different shape. According to an exemplary embodiment, a top surface 819 of ribs 818 (which may be curved like ribs 718 of FIG. 15) may be dished so that top surface 819 is not flush with a surface 813 of interface disk 810, as shown in FIG. 16. Thus, ribs 818 may have a dished profile relative to surface 813. For example, a distance between top surface 819 of ribs 818 and surface 813 may increase in a direction from an outer edge 819 of depression 816 to a central aperture 817. As a result, when a user engages depression 816, such as by inserting a fingertip or a finger-shaped object, such as, for example, a stylus, pencil, or other specially-designed tool having a configuration similar to a finger, within depression 816, turning of interface disk 810 in direction 840 in FIG. 16 is facilitated because the fingertip or object may wind down into the spiral formed by ribs 818 and be inserted deeper into depression 816. Although edge 820 of interface disk 810 may lack a knurled edge, as shown in FIG. 16, edge 820 may instead be knurled, as shown in FIGS. 11 and 12.

Figure 17:
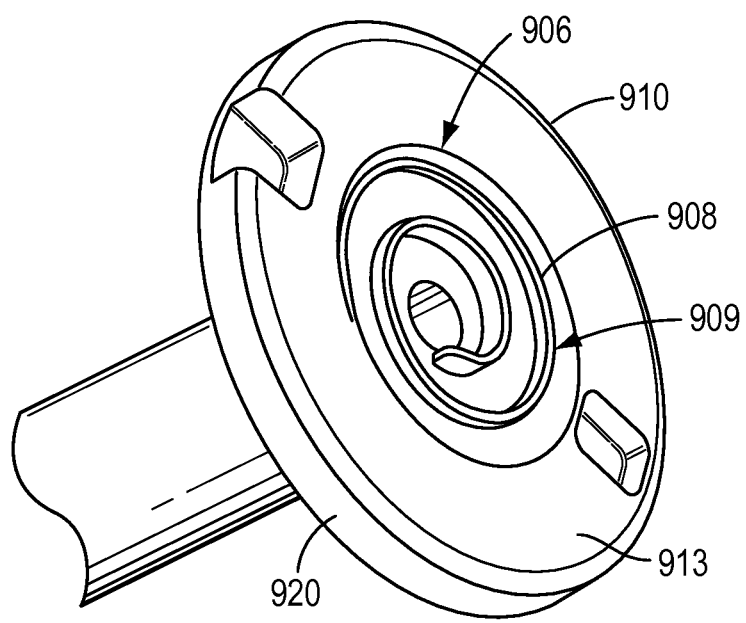
FIG. 17 is a perspective view of an actuation input mechanism, according to an exemplary embodiment.

As shown in the exemplary embodiments of FIGS. 16 and 17, a depression of an interface disk may include a plurality of ribs arranged in a spiral pattern. According to another exemplary embodiment, an interface disk 910 may include a depression 906 having a single rib 908 arranged in a spiral pattern, as shown in FIG. 17. Similar to the exemplary embodiment of FIG. 15, a top surface 909 of rib 908 may be flush with surface 913 of interface disk 910. According to another exemplary embodiment, the interface disk 1010 of FIG. 18 may include a depression 1008 with a single rib 1008 having a top surface 1009 that is dished relative to surface 1013 of interface disk 1010 (e.g., rib 1008 may have a dished profile relative to surface 1013), similar to the exemplary embodiment of FIG. 16. Although edges 920 and 1020 of interface disks 910 and 1010 may lack a knurled edge, as shown in FIGS. 17 and 18, edges 920 and 1020 may instead be knurled, as shown in FIGS. 11 and 12.

According to an exemplary embodiment, an interface disk of a force transmission mechanism may include gripping features that extend above a surface of the interface disk. Turning to FIG. 19, an interface disk 1110 is shown that includes a central aperture 1107 and projections 1108 that extend from a surface 1102 of interface disk 1110. Projections 1108 may act as gripping features, such as for a user to manually engage during a cleaning procedure, and may also serve as projections to engage with corresponding slots on driven disks of an actuation interface assembly, as described above with regard to the exemplary embodiment of FIG. 4. Although edge 1120 of interface disk 1110 may lack a knurled edge, as shown in FIG. 19, edge 1120 may instead be knurled, as shown in FIGS. 11 and 12.

Interface disks of the various exemplary embodiments described herein may be made of molded plastic. However, the various exemplary embodiments are not limited solely to molded plastic but may include additional materials, such as to facilitate gripping of the interface disks by a user. According to an exemplary embodiment, interface disks may be made of plastic overmolded with a second material, such as a material that is more compliant than the plastic. The second material may facilitate gripping of the interface disk due to its compliant nature. The compliant material may be, for example, an elastomer, such as rubber. Turning to FIG. 20, an interface disk 1210 is shown that includes slots 1212, a depression 1216 (which may be arranged according to the various exemplary embodiments described herein), with the interface disk 1210 including a main body 1240 formed by a first material, such as a plastic, and a second overmolded material 1230 more compliant than the first material 1240 (a portion of second material 1230 being removed in FIG. 20 to reveal the first material 1240 underneath). Main body 1240 may be completely covered by material 1230 as indicated in the exemplary embodiment of FIG. 20, or main body 1240 may be partially covered by material 1230, such as by applying material 1230 as discrete features, such as ribs, spirals, or dots. Although edge 1220 of interface disk 1210 may lack a knurled edge, as shown in FIG. 20, edge 1220 may instead be knurled, as shown in FIGS. 11 and 12.

Although some interface disks (e.g., interface disk 240 of FIG. 11) of some exemplary embodiments have been depicted and/or described as having a knurled edge continuously around a circumference of the interface disk, persons having ordinary skill in the art will appreciate that a knurled edge of an interface disk may extend along only one or more portions of an edge of an interface disk. For example, the knurled edge of an interface disk may be discontinuous and extend along one or more portions of the edge of the interface disk in the various exemplary embodiments described herein.

By providing a surgical instrument with interface disks of actuation input mechanisms with gripping features according to the various exemplary embodiments described herein, manual actuation of the interface disks by a user during a cleaning procedure may be facilitated. Thus, a user may actuate a functionality of the instrument by manually actuating an interface disk instead of grasping an instrument component (e.g., an end effector) with their hand.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. An actuation input mechanism for a teleoperated surgical instrument, the actuation input mechanism comprising:
    an interface structure engageable with a drive structure of an actuation interface assembly of a teleoperated surgical system so as to be driven by the drive structure; and
    a shaft connected to the interface structure and rotatably driven by the interface structure;
    wherein the interface structure comprises a depression shaped and sized to receive a fingertip, and
    wherein the interface structure comprises one or more gripping features disposed in the depression.

2. The actuation input mechanism of claim 1, wherein the one or more gripping features comprise one or more ribs.

3. The actuation input mechanism of claim 2, wherein the one or more ribs extend radially from a central region of the depression.

4. The actuation input mechanism of claim 3, wherein the one or more ribs are substantially straight.

5. The actuation input mechanism of claim 2, wherein the interface structure has a disk shape.

6. The actuation input mechanism of claim 5, wherein the depression is located in a planar surface of the disk shape, and wherein the one or more ribs have a profile substantially flush with the planar surface.

7. The actuation input mechanism of claim 5, wherein the depression is located in a planar surface of the disk shape, and wherein the ribs have a dished profile relative to the planar surface.

8. The actuation input mechanism of claim 3, wherein an end of the one or more ribs proximate to the central region of the depression is rounded.

9. The actuation input mechanism of claim 3, wherein an end of the one or more ribs proximate to the central region is spaced from a central aperture located in the central region.

10. The actuation input mechanism of claim 2, wherein the one or more ribs are arranged in a spiral pattern.

11. The actuation input mechanism of claim 1, wherein the one or more gripping features is a single, continuous rib having a spiral shape.

12. The actuation input mechanism of claim 1, wherein the interface structure comprises a knurled edge.

13. The actuation input mechanism of claim 1, wherein the interface structure comprises at least one slot configured to receive a projection of the drive structure of the actuation interface assembly to drive the interface structure.

14. The actuation input mechanism of claim 1, wherein the interface structure comprises a first material and a second material overmolded onto the first material, wherein the second material is more compliant than the first material.

15. The actuation input mechanism of claim 1, wherein the shaft comprises an output section configured to be coupled to a drive member to actuate a surgical instrument component.

16. The actuation input mechanism of claim 15, wherein the output section comprises gear teeth, a rack, screw threads, or grooves.

17. The actuation input mechanism of claim 1, wherein the interface structure is manually driveable via a finger.

18. A surgical instrument for a teleoperated surgical system, the instrument comprising:
    an instrument shaft;
    an end effector coupled to a first end of the instrument shaft; and
    a force transmission mechanism coupled to a second end of the instrument shaft opposite the first end, the force transmission mechanism comprising an actuation input mechanism configured to transmit drive forces to actuate the surgical instrument, wherein the actuation input mechanism comprises:
        an interface structure engageable with a drive structure of an actuation interface assembly of the teleoperated surgical system so as to be driven by the drive structure; and
        an actuation shaft connected to the interface structure, the actuation shaft being rotatably driven by the interface structure;
        wherein the interface structure comprises a depression shaped and sized to receive a fingertip, and wherein the interface structure comprises one or more gripping features disposed in the depression.

19. The surgical instrument of claim 18, further comprising a wrist, the end effector being coupled to the instrument shaft by the wrist.

20. The surgical instrument of claim 19, wherein the force transmission mechanism further comprises a second actuation input mechanism comprising an interface structure and an actuation shaft connected to the interface structure, wherein the interface structure is engageable with a second drive structure of the actuation interface assembly to be driven by the drive structure and actuate the wrist.

21. The surgical instrument of claim 18, wherein the actuation shaft comprises an output section configured to be coupled to a drive member to actuate the end effector.

22. The surgical instrument of claim 21, wherein the output section comprises gear teeth, a rack, screw threads, or grooves.

23. The surgical instrument of claim 18, wherein the one or more gripping features comprise one or more ribs.

24. The surgical instrument of claim 18, wherein the interface structure comprises a knurled edge.

25. The surgical instrument of claim 24, wherein the force transmission mechanism comprises a cutout to provide access to the knurled edge.

26. A method of cleaning a surgical instrument of a teleoperated surgical system, the method comprising:
    positioning a finger-shaped object into a depression of an interface structure of an actuation input mechanism, wherein the depression is sized and shaped to receive the finger-shaped object, and wherein the interface structure is engageable to be driven by a drive structure of an actuation interface assembly of the teleoperated surgical system to actuate one or more components of the surgical instrument;

driving the actuation input mechanism by manipulating the interface structure using the finger-shaped object received in the depression; and actuating one or more components of the surgical instrument in response to the driving for a cleaning procedure.

27. The method of claim 26, the depression further comprising one or more gripping features, wherein the driving the actuation input mechanism comprises manipulating the interface structure via the one or more gripping features.

28. The method of claim 27, wherein the one or more gripping features comprise ribs.

29. The method of claim 27, wherein the finger-shaped object is a user's finger.

* * * * *